United States Patent
Sutton et al.

(10) Patent No.: US 12,108,792 B2
(45) Date of Patent: Oct. 8, 2024

(54) AEROSOL PROVISION SYSTEM

(71) Applicant: Nicoventures Trading Limited, London (GB)

(72) Inventors: Joseph Sutton, London (GB); Terry Lee Angell, London (GB)

(73) Assignee: NICOVENTURES TRADING LIMITED, London (GB)

( * ) Notice: Subject to any disclaimer, the term of this patent is extended or adjusted under 35 U.S.C. 154(b) by 377 days.

(21) Appl. No.: 17/604,317

(22) PCT Filed: Apr. 9, 2020

(86) PCT No.: PCT/GB2020/050920
§ 371 (c)(1),
(2) Date: Oct. 15, 2021

(87) PCT Pub. No.: WO2020/212690
PCT Pub. Date: Oct. 22, 2020

(65) Prior Publication Data
US 2022/0287364 A1    Sep. 15, 2022

(30) Foreign Application Priority Data
Apr. 17, 2019   (GB) .................................... 1905442

(51) Int. Cl.
*A24F 40/42*   (2020.01)
*A24F 40/60*   (2020.01)
*A24F 40/85*   (2020.01)

(52) U.S. Cl.
CPC .............. *A24F 40/42* (2020.01); *A24F 40/60* (2020.01); *A24F 40/85* (2020.01)

(58) Field of Classification Search
CPC .......... A24F 40/42; A24F 40/40; A24F 40/60; A24F 40/85; A24F 15/015; A24F 7/00
(Continued)

(56) References Cited

U.S. PATENT DOCUMENTS 10,779,573 B2 *   9/2020   Rose .......................... H05B 3/44
10,834,965 B2 *  11/2020   Zhu ............................ H05B 3/48
(Continued)

FOREIGN PATENT DOCUMENTS

WO    WO2018/0113511 A1    6/2018

OTHER PUBLICATIONS

International Search Report and Written Opinion for International Application No. PCT/GB2020/050920, dated Jun. 16, 2020, 12 pages.
(Continued)

*Primary Examiner* — Harshad C Patel
(74) *Attorney, Agent, or Firm* — Husch Blackwell (57) ABSTRACT

An aerosol provision cartridge (30) for an aerosol provision system (10). The cartridge (30) comprises a refillable chamber (100) for aerosol precursor material, the chamber (100) comprising a first opening (102) and a second opening (104), each opening (102;104) allowing for access into the chamber (100). Each opening (102;104) is covered by a respective cap (130;132) which is configured to be uncoupled from the chamber (100) for allowing access to the opening (102;104). The cartridge (30) is configured such that each cap (130; 132), when coupled to the chamber (100), requires at least two different actions (A1;A2) to be uncoupled from the chamber (100). The first or second action (A1;A2) may each include, but are not limited, to: rotating; pulling; pushing; or unlatching.

30 Claims, 8 Drawing Sheets

(58) Field of Classification Search
USPC .......................................................... 131/329
See application file for complete search history.

(56) References Cited

U.S. PATENT DOCUMENTS

| | | | | |
|---|---|---|---|---|
| 10,834,966 B2* | 11/2020 | Zhu | ...................... | A24B 15/167 |
| 11,206,868 B2* | 12/2021 | Alarcon | ................... | H05B 3/03 |
| 11,660,403 B2* | 5/2023 | Atkins | .................... | A24F 40/40 |
| | | | | 131/271 |
| 2015/0007836 A1* | 1/2015 | Li | ........................... | A24F 40/46 |
| | | | | 131/329 |
| 2015/0164146 A1* | 6/2015 | Li | ........................ | A24F 40/485 |
| | | | | 392/395 |
| 2016/0366943 A1* | 12/2016 | Li | ........................... | A24F 40/42 |
| 2017/0049153 A1* | 2/2017 | Guo | ........................ | H05B 3/18 |
| 2019/0053544 A1* | 2/2019 | Yamada | ................ | A24F 40/485 |
| 2019/0099561 A1 | 4/2019 | Nettenstrom | | |
| 2020/0187562 A1* | 6/2020 | Rogan | ..................... | A24F 40/40 |
| 2022/0287364 A1* | 9/2022 | Sutton | ................. | A61M 11/042 |

OTHER PUBLICATIONS

International Preliminary Report on Patentability for Application No. PCT/GB2020/050920 mailed Oct. 28, 2021, 7 pages.

* cited by examiner

AEROSOL PROVISION SYSTEM

CROSS-REFERENCE TO RELATED APPLICATIONS

This application is a National Phase entry of PCT Application No. PCT/GB2020/050920, filed Apr. 9, 2020, which application claims the benefit of priority to GB 1905442.8, filed Apr. 17, 2019, the entire disclosures of which are incorporated herein by reference.

FIELD

The present disclosure relates to aerosol provision cartridges, and systems and methods relating thereto.

BACKGROUND

Aerosol provision systems such as e-cigarettes generally contain, amongst other parts, an aerosol provision cartridge which comprises a reservoir of an aerosol precursor material, such as a source liquid, typically including nicotine, from which an aerosol is generated, e.g. through vaporisation or other means. The aerosol provision cartridge may also comprise an aerosol generating component, such as a heater, which is fluidly connected to the aerosol precursor material contained in the reservoir. When a user inhales on the device, the aerosol generating component is activated to vaporise an amount of the aerosol precursor material. More particularly, such devices are usually provided with one or more air inlet holes located away from a mouthpiece of the system. When a user sucks on the mouthpiece, air is drawn in through the inlet holes and past the aerosol generating component. There is a flow path connecting between the aerosol generating component and an opening in the mouthpiece so that air drawn past the aerosol generating component continues along the flow path to the mouthpiece opening, carrying some of the aerosol produced from the aerosol generating component with it. The aerosol-carrying air exits the aerosol provision system through the mouthpiece opening for inhalation by the user.

Typical aerosol generating components comprise a heater. The aerosol precursor material is generally arranged within the system such that it can access the aerosol generating component. For example, it may be that the aerosol generating component is a wire which is heated during use of the device. As a result of the contact between the aerosol precursor material and the wire, when the wire is heated during use the aerosol precursor material is vaporised and subsequently condenses into an aerosol which is then inhaled by the user.

The means by which the aerosol precursor material can contact the wire may vary. It is not uncommon for the aerosol precursor material to be held freely in a refillable tank or other refillable storage region, and then directly fed to the heating wire (which may itself include a wick to assist in holding the aerosol precursor material in proximity to the wire).

To inhibit leakage of aerosol precursor material from such a refillable tank or storage region, and also to inhibit inadvertent access to such aerosol precursor material-holding regions by the user, it would be desirable to provide an aerosol provision cartridge which is configured accordingly.

SUMMARY

In a first aspect there is provided an aerosol provision cartridge for an aerosol provision system, wherein the cartridge comprises a refillable chamber for aerosol precursor material, the chamber comprising a first opening and a second opening, each opening allowing for access into the chamber, wherein each opening is covered by a respective cap which is configured to be uncoupled from the chamber for allowing access to the opening, wherein the cartridge is configured such that each cap, when coupled to the chamber, requires at least two different actions to be uncoupled from the chamber.

In a further aspect there is provided an aerosol provision system configured to receive the aerosol provision cartridge as described above.

In a further aspect there is provided an aerosol provision system comprising the aerosol provision cartridge as described above.

In yet a further aspect there is provided a method of accessing a chamber for aerosol precursor material comprised in an aerosol provision cartridge for an aerosol provision system, wherein the aerosol provision cartridge comprises the chamber for aerosol precursor material, the chamber comprising a first opening and a second opening each allowing access into the chamber, wherein each opening is covered by a respective cap which is configured to be uncoupled from the chamber for allowing access to the opening, wherein the aerosol provision cartridge is configured such that each cap, when coupled to the chamber, requires at least two different actions to be uncoupled from the chamber; wherein the method comprises the steps of:
performing a first action on one of the caps; and
performing a second action on the cap;
wherein the first action is different to the second action.

The approach described herein is not restricted to specific embodiments such as those set out below, but includes and contemplates any appropriate combinations of features presented herein. For example, an electronic aerosol provision system may be provided in accordance with the approach described herein which includes any one or more of the various features described below as appropriate.

BRIEF DESCRIPTION OF THE DRAWINGS

Various embodiments will now be described in detail by way of example only with reference to the following drawings.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision cartridge which may form part of an aerosol provision system, such as an e-cigarette. Throughout the following description the term "e-cigarette" is sometimes used; however, this term may be used interchangeably with aerosol (vapor) provision system, or vapor provision device. Further, term "aerosol provision cartridge" may also be referred to as cartomizer, clearomiser or tank, as such terms are common in the field of aerosol provision systems such as e-cigarettes.

Figure 1:
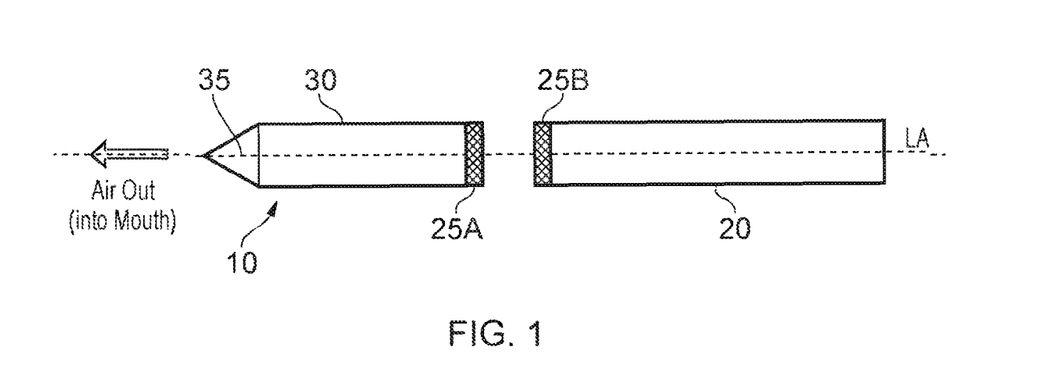
FIG. 1 is a schematic (exploded) diagram of an aerosol provision system such as an e-cigarette in accordance with some embodiments.

FIG. 1 is a schematic diagram of an aerosol/vapor provision system such as an e-cigarette 10 in accordance with some embodiments (not to scale). The e-cigarette has a generally cylindrical shape, extending along a longitudinal axis indicated by dashed line LA, and comprises two main components, namely a body 20 and a cartomizer 30. The cartomizer includes an internal chamber containing an aerosol precursor material storage region comprising an aerosol precursor material, which may be a liquid, from which an aerosol is to be generated, and an aerosol generating component. The cartomizer 30 further includes a mouthpiece 35 having an opening through which a user may inhale the aerosol produced by the aerosol generating component. In this regard, reference to an "aerosol generating component" refers to a component which generates an aerosol either directly or indirectly. For example, where the aerosol generating component is a heater, aerosol precursor material may be evaporated and subsequently condense to form an aerosol.

The aerosol precursor material storage region for the aerosol precursor material may comprise a foam matrix or any other structure, such as a wadding, within a housing for retaining the aerosol precursor material until such time that it is required to be delivered to the aerosol generating component. Alternatively, the aerosol precursor material storage region may simply be a reservoir which an amount of "free liquid" contained therein. The aerosol precursor material storage region is preferably "open" such that it is configured to be re-filled by the user. This "open" configuration can generally be achieved by using a mouthpiece or other component that seals the aerosol precursor material storage region, but which can be opened such that access to the aerosol precursor material storage region is provided.

The aerosol generating component includes a heater for vaporising the aerosol precursor material to form the aerosol. The aerosol generating component may further include a wick or similar facility to transport a small amount of the aerosol precursor material from the storage region to a heating location on or adjacent the heater.

The body 20 includes an electrical power source, for example a rechargeable, or replaceable cell or battery, to provide power for the e-cigarette 10 and a circuit board for generally controlling the e-cigarette. In use, when the heater receives power from the electrical power source, as controlled by the circuit board, the heater vaporises the aerosol precursor material at the heating location to generate the aerosol, and this is then inhaled by a user through the opening in the mouthpiece. The aerosol is carried to the mouthpiece along an air channel that connects the aerosol generating region to the mouthpiece opening as a user inhales on the mouthpiece.

In this particular example, the body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector on the body 20 that is used to connect to the cartomizer also serves as a socket for connecting a charging device (not shown) when the body is detached from the cartomizer 30. The other end of the charging device can be plugged into an external power supply, for example a USB socket, to charge or to re-charge the electrical power source in the body of the e-cigarette. In other implementations, a cable may be provided for direct connection between the electrical connector on the body and the external power supply.

In connection with this, in order to allow for connection with the body 20 (both mechanically and electrically) the cartomizer 30 generally contains one or more metallic components. For example, these components may be screw thread rings, electrodes, or intermediate supporting members (all not shown). When assembled, such metallic components allow for the cartomizer 30 to be connected to the body 20 in a manner which supports the aerosol generating component in the aerosol generating region, allows for the provision of electrical current to the aerosol generating component, and allows for airflow to travel into the aerosol generating region so that it may collect the vapor/aerosol produced therein and deliver it to the user.

The e-cigarette 10 is provided with one or more holes (not shown in FIG. 1) for air inlet. These holes connect to an air running passage through above mentioned metallic components of the e-cigarette 10 to the mouthpiece 35. The air passage includes a region around the aerosol generating region and a section comprising an air channel connecting from the aerosol generating region to the opening in the mouthpiece.

When a user inhales through the mouthpiece 35, air is drawn into this air passage through the one or more air inlet holes, which are suitably located on the outside of the e-cigarette. This airflow (or the resulting change in pressure) is detected by a pressure sensor (as an example of an input means) that in turn activates the aerosol generating component (heater in this case) to vaporise a portion of the aerosol precursor material to generate the aerosol. The airflow passes through the air passage, and combines with the aerosol in the region around the aerosol generating region, and the resulting aerosol then travels along the air channel connecting from the aerosol generating region to the mouthpiece 35 to be inhaled by a user. The cartomizer 30 may be detached from the body 20 and disposed of when the supply of aerosol precursor material is exhausted (and replaced with another cartomizer if so desired), though preferably the cartomizer is refillable.

It will be appreciated the e-cigarette 10 shown in FIG. 1 is presented by way of example, and various other implementations can be adopted. For example, in some embodiments, the cartomizer 30 is provided as two separable components, namely a cartridge comprising the aerosol precursor material storage region and mouthpiece (which can be replaced/refilled when the aerosol precursor material from the reservoir is exhausted), and a vaporiser/aerosol generating component comprising a heater (which is generally retained). In some embodiments, the aerosol generating component may itself be replaceable.

Figure 2A:
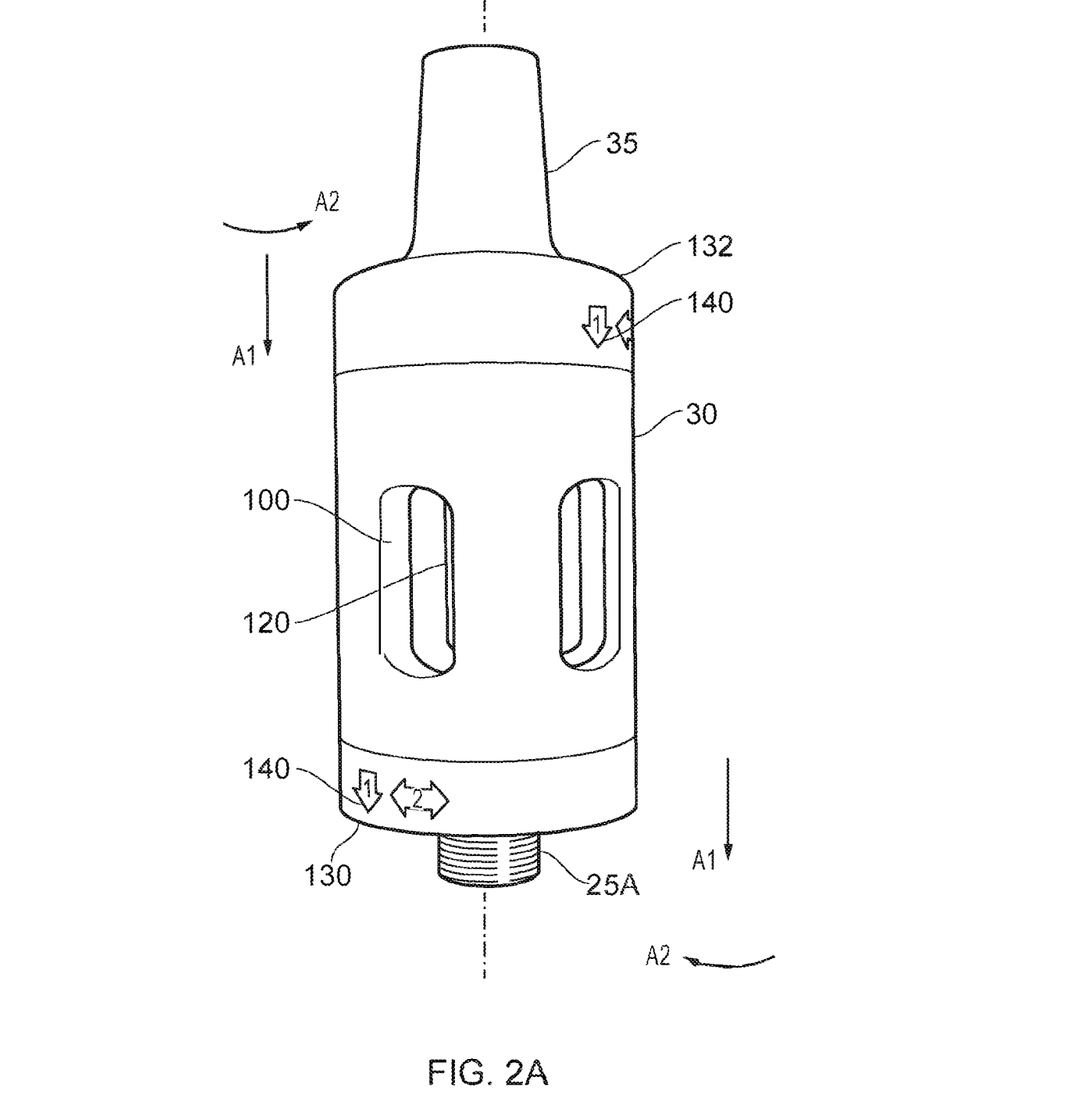
FIG. 2A is a perspective view of an exemplary aerosol provision cartridge for an aerosol provision system.
Figure 2B:
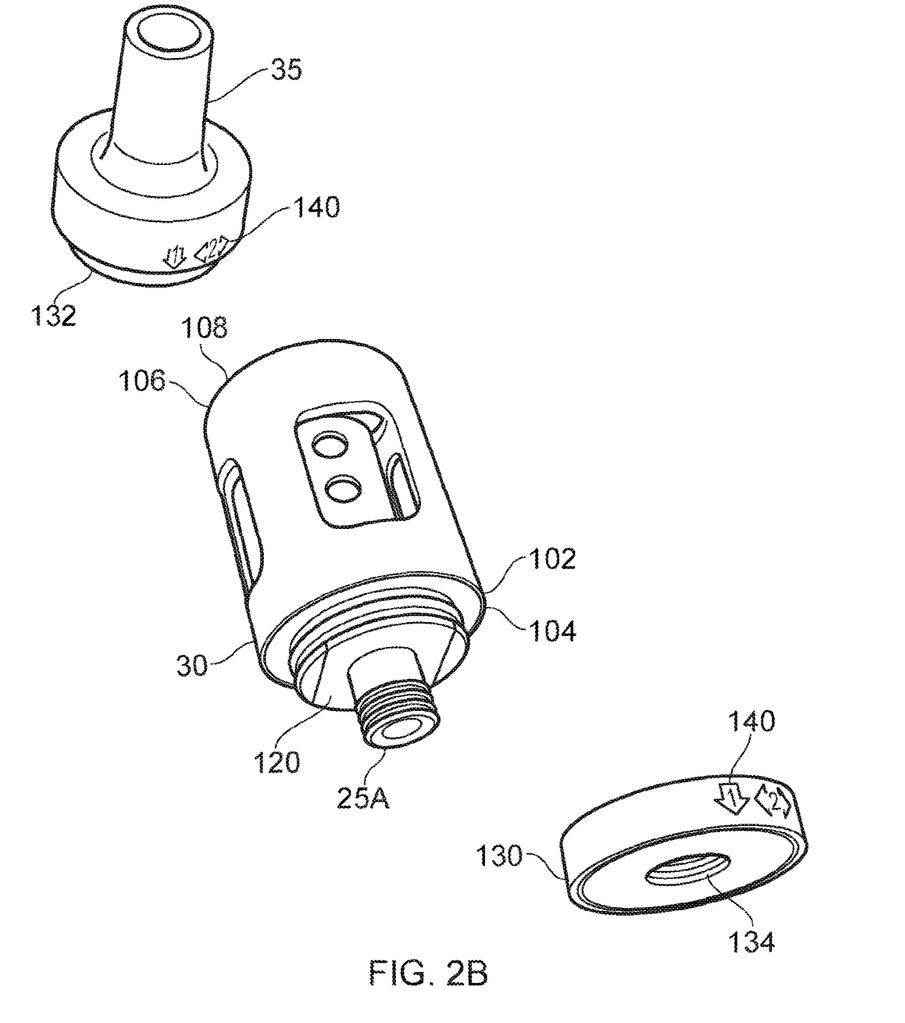
FIG. 2B is an exploded perspective view the aerosol provision cartridge from FIG. 2A.

With reference to FIGS. 2A and 2B, there is shown an embodiment of cartomizer 30. The cartomizer 30 comprises a refillable chamber 100 for the aerosol precursor material. The chamber 100 is substantially cylindrical and defines a first open end 102 forming a first opening 104 into the chamber, and defines a second open end 106 forming a second opening 108 into the chamber. Each of the first and second opening 104;108 allow for the insertion of aerosol precursor material into the chamber as will be described.

An aerosol generating component 120 is located inside the chamber 100 for vaporising a portion of the aerosol precursor material contained therein, as described in connection with FIG. 1.

A first cap 130 and a second cap 132 respectively cover the first opening 102 and the second opening 108 of the chamber 100. The first cap 130 is shown in FIGS. 2A and 2B as comprising an orifice 134 through which the aerosol generating component 120 projects when the first cap 130 is coupled to the chamber 100. The second cap 132 defines the mouthpiece 35 for the cartomizer 30, and is configured to receive the aerosol generated by the aerosol generating component 120 for delivery to the user.

In the assembled state shown in FIG. 2A, aerosol precursor material is configured to be held inside the chamber 100 between the first and second end caps 130;132 and around the aerosol generating component 120.

To refill the aerosol precursor material contained inside the chamber 100, at least one of end caps 130;132 is uncoupled from the chamber 100, and the aerosol precursor material then inserted into the chamber through the exposed opening 104;108.

In some embodiments, to allow for better access to the aerosol generating component 120, the aerosol generating component 120 may be removable through at least one of the first and second openings 102;104 when the first cap 130 for the first opening 102 and the second cap 132 for the second opening 104 are uncoupled from the chamber 100. In other embodiments, the aerosol generating component 120 may be removable through each of the first and second openings 102;104 when the first cap 130 for the first opening 102 and the second cap 132 for the second opening 104 are uncoupled from the chamber 100.

To inhibit leakage of aerosol precursor material from the chamber 100, each cap 130;132, when coupled to the chamber, may require at least two different actions, which may in some embodiments be in two different directions, to be uncoupled from the chamber 100. In that regard, in the case of the first cap 134 as shown in FIGS. 2A and 2B, the first cap 130 must be pulled outwardly away from the aerosol generating component 120 as a first action A1 from the user in a first linear direction, and then rotated as a second action A2 from the user in a second clockwise direction to be uncoupled from the chamber 100. Unless both actions are performed, for instance the user tries to rotate the first cap 130 without first pulling it, the first cap 130 will not uncouple from the chamber 100.

In the case of the second cap 132 for the embodiment shown in FIGS. 2A and 2B, the second cap 132 must be pushed inwardly by the user towards the aerosol generating component 120 as a first action A1 in a first linear direction, and then rotated as a second action A2 in a second anti-clockwise direction to be uncoupled from the chamber 100. Again, unless both the first and second actions are performed, the second cap 134 remains coupled to the chamber 100. Once the first cap 130 and the second cap 132 are uncoupled from the chamber 134, the aerosol generating component 120 can be removed from the chamber 100.

In each of the above cases, it can be seen that the first action required by the user for each cap is different to the second action for the cap (e.g., a pull/push action as the first action followed by a rotation action as the second action). In that regard, the first and second actions are not the same type of action performed twice. In some embodiments, the direction of the first action may also be different to that of the second action (e.g., a linear direction for the first action as opposed to a clockwise/anti-clockwise direction for the second action). In this way, the requirement for all of the caps from the cartomizer 30 to each require at least two different actions from the user, and in some embodiments also actions performed in different directions, helps inhibit leakage of aerosol precursor material from the chamber 100 by rendering it less likely that the chamber will be accessed if accidentally knocked/touched by the user (e.g. when the cartomizer is located in a pocket of a user).

In some embodiments, the required first and second actions or direction of these actions may be indicated by a visual indicia on the cartomizer at an appropriate location to inform the user as to how to uncouple the cap 130;132 from the chamber 100. In the case of the cartomizer 30 shown in FIGS. 2A and 2B, the visual indicia 140 is series of numbered arrows on each cap, wherein the numbered arrows indicate the action and direction for each of the first action and the second action for the cap.

In some embodiments, the at least two actions for the cap for the first opening may be different from the at least two actions for the cap for the second opening, for instance as in the embodiment shown in FIGS. 2A and 2B where the actions for the first cap 130 are pull/rotate in contrast with the actions for the second cap 132 which are push/rotate.

Figure 2C:
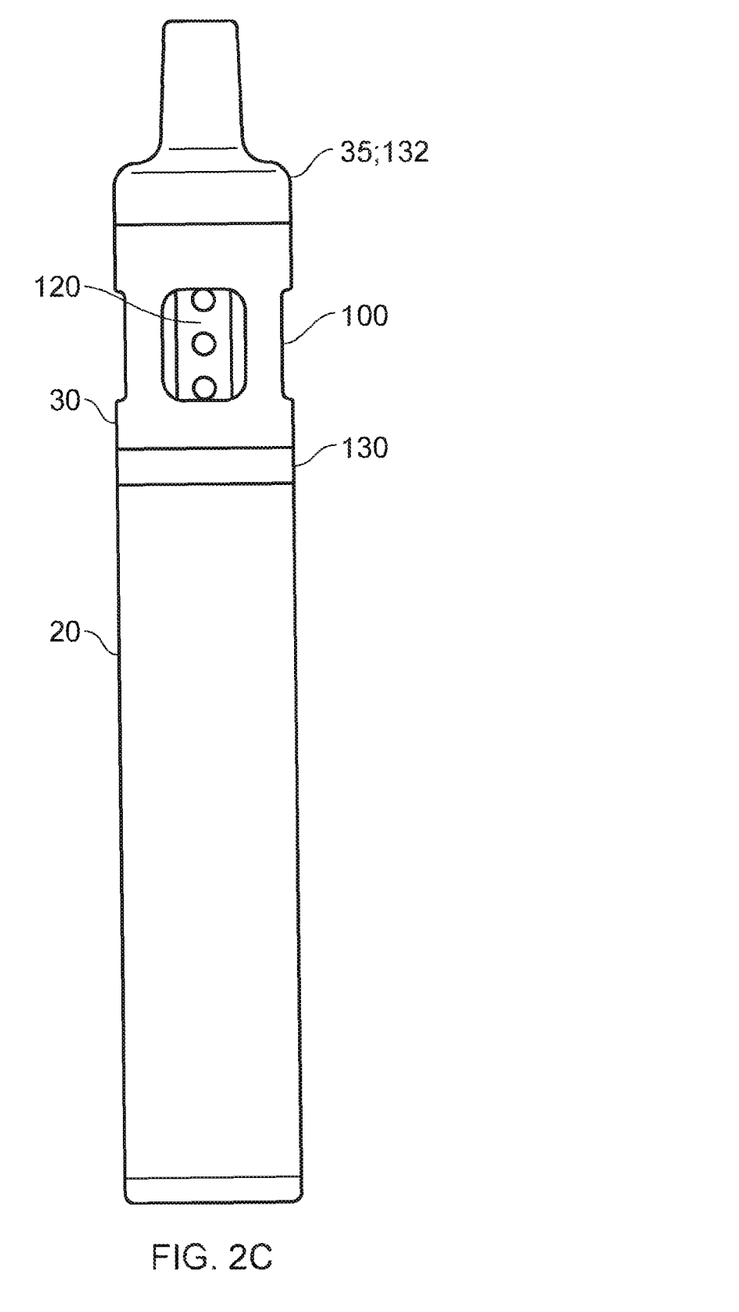
FIG. 2C is a side view of the aerosol provision cartridge from FIG. 2A when attached to a body to form an aerosol provision system.

During use of the cartomizer 30 shown in FIGS. 2A and 2B, through the connection 25A/25B, the cartomizer 30 is attached to the body 20 such that the first cap 130 for the first opening abuts the body 20, as shown in FIG. 2C. In some embodiments, in this attached position the body 20 is configured to push the first cap 130 against the first pulling action of the cap, which further reduces the likelihood of the first cap 130 being inadvertently opened at the first opening 104 during use of the aerosol provision system.

It will be appreciated that any combination of different actions can be used to control the coupling of each of the caps to the chamber 100. For instance, each of the first and second actions for a given cap 130;132 may comprise rotating; pulling; pushing; or unlatching. This list is not exhaustive.

Figure 3:
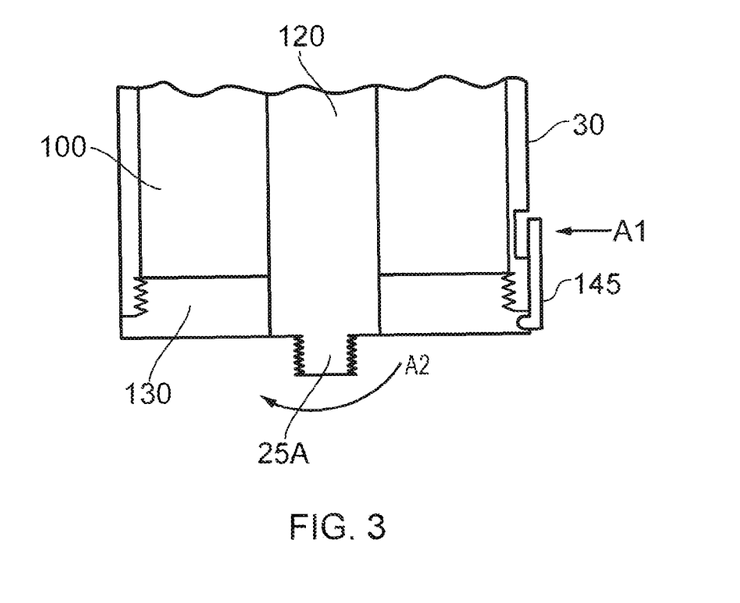
FIG. 3 is a cross-sectional view showing a portion of an embodiment of aerosol provision cartridge.

For instance, in one embodiment one of the first and second actions may be an unlatching action, as shown in the embodiment from FIG. 3. In this embodiment, the cartomizer 30 comprises a latch 142 which is biased into engagement with the first cap 130, which is screwed into engagement with the chamber 100. When the latch 142 is engaged with the first cap 130, any rotation of the first cap 130 will not cause it to uncouple from the chamber 100. Instead, the first cap 130 is uncoupled by first unlatching the latch 142 out from engagement from the first cap 130 as a first action A1 in a first, linear, direction, and then rotating the first cap 130 as the second action A2 in a second, clockwise, direction to allow it to uncouple from the chamber 100.

In accordance with some embodiments, a biasing means may be provided for biasing one or more of the caps towards the position where the cap is coupled to the chamber. In that way, the provision of the biasing means may make it less likely that the cap will become uncoupled if momentarily knocked/touched by the user. As required, the biasing means may be provided between the first cap 130 and the chamber 100, or between the second cap 132 and the chamber 100.

Figure 4A:
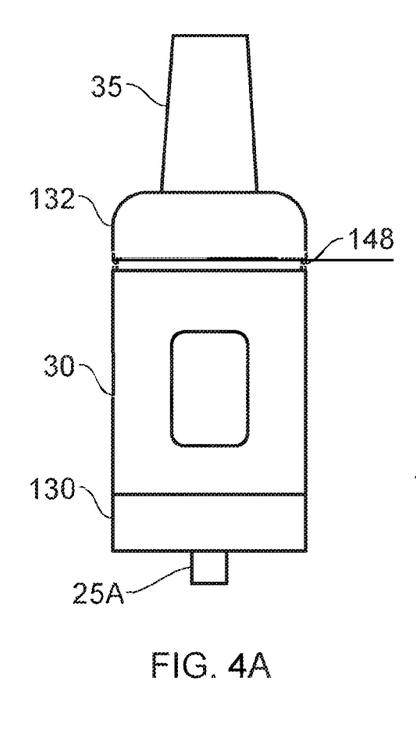
FIG. 4A is a side view of an exemplary aerosol provision cartridge for an aerosol provision system in a first state.
Figure 4B:
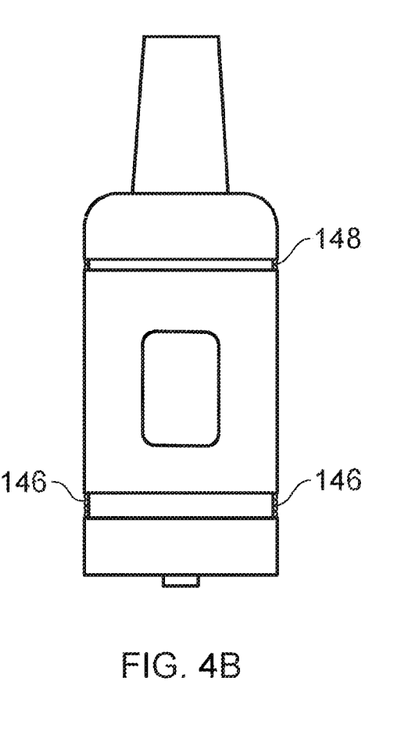
FIG. 4B is a side view of the aerosol provision cartridge from FIG. 4A when in a second state.
Figure 4C:
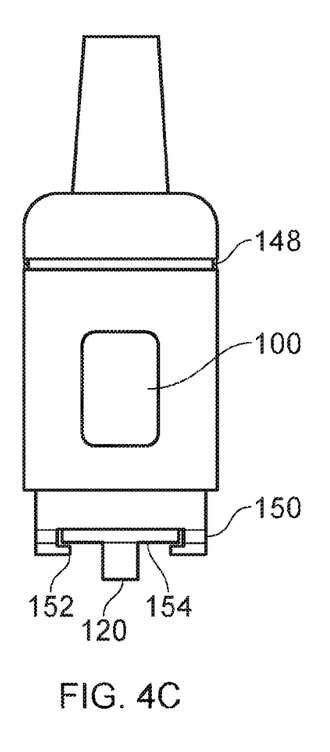
FIG. 4C is a side view of the aerosol provision cartridge from FIG. 4A when in a third state.

An example of such embodiments is illustrated in FIGS. 4A-4C, which is based on the embodiment shown in FIGS. 2A and 2B. There, a first biasing means 146 in the form of a first spring is positioned between the first cap 130 and the chamber 100, such that a biasing force from the first biasing means 146 acts against the first pulling action required to uncouple the first cap 130 from the chamber 100. A second biasing means 148 in the form of a second spring is positioned between the second cap 132 and the chamber 100 to similarly provide a biasing force which acts against the first pushing action required to uncouple the second cap 130 from the chamber 100.

In some embodiments, as shown in the embodiments of FIGS. 4A-4C, a retaining means 150 may be provided for holding the aerosol generating component 120 inside the chamber 100 even when the first cap 130 has been uncoupled from the chamber 100. In such embodiments, the retaining means may comprise a shoulder 152 which engages an end portion 154 of the aerosol generating component 120. The shoulder 152 may be disengaged from the end portion 154 of the aerosol generating component 120 in a number of different configurations, for instance by taking the form of a resilient component which may be deflected outwardly and out from engagement with the end portion 154 of the aerosol generating component 120. In another configuration, the shoulder 152 may be detachable from the rest of the chamber 100, such to allow the shoulder 152 to disengage from the end portion 154 of the aerosol generating component 120.

Figure 5A:
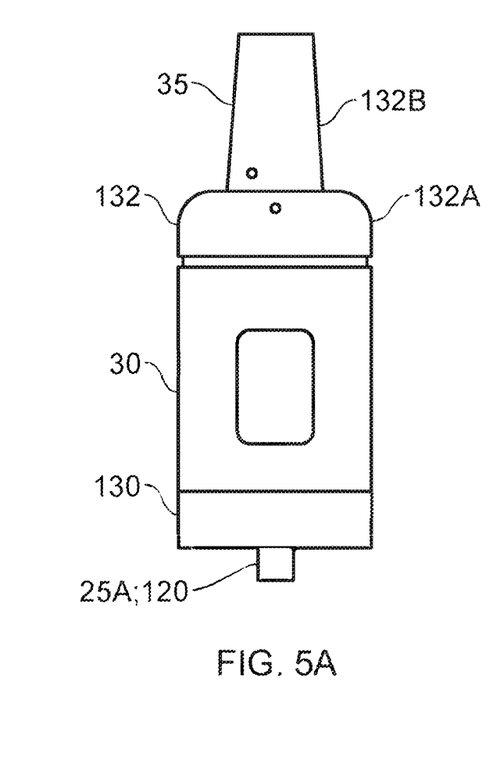
FIG. 5A is a side view of another exemplary aerosol provision cartridge for an aerosol provision system when in a first state.
Figure 5B:
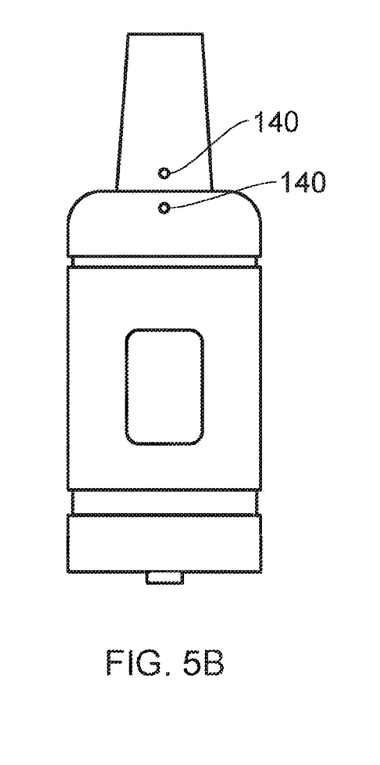
FIG. 5B is a side view of the aerosol provision cartridge from FIG. 5A when in a second state.
Figure 5C:
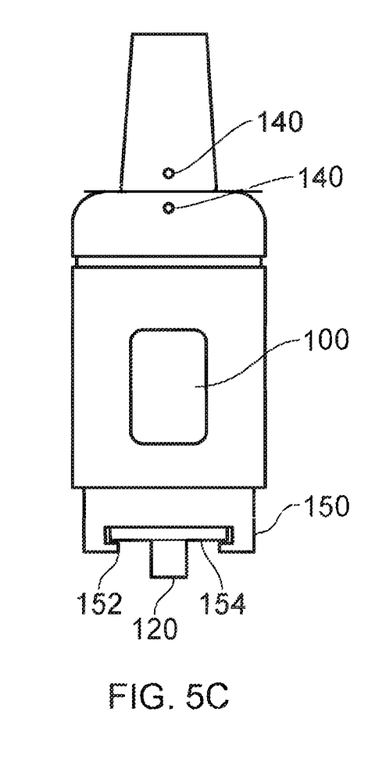
FIG. 5C is a side view of the aerosol provision cartridge from FIG. 5A when in a third state.

In accordance with some embodiments, there may be provided an alignment mechanism configured to prevent one or more of the caps from being uncoupled from the chamber unless the cap is rotated to a predetermined position with respect to the chamber. An example of such an alignment mechanism is illustrated in the embodiment of FIGS. 5A-5C, which is similar to the embodiments of FIGS. 4A-4C. The function of the alignment mechanism is to reduce the likelihood of the chamber being accessed through an accidental uncoupling of the first cap 130 or the second cap 132 with respect to the chamber 100, by necessitating these caps align at a particular rotational position before they can be uncoupled. The alignment mechanism from the embodiment of FIGS. 5A-5C comprises the second cap 132 comprising a first base portion 132A that is rotatable with respect to a mouthpiece portion 132B (which defines the mouthpiece 35) of the second cap 132. In that embodiment, to uncouple the second cap 132 from the chamber 100, the second cap 132 must be pushed inwardly by the user towards the aerosol generating component 120 as a first action A1 in a first linear direction, and then rotated as a second action A2 in a second anti-clockwise direction. In addition, the second cap 132 can then only be uncoupled if the base portion 132A and the mouthpiece portion 132B of the second cap 132 are rotated to a predetermined position with respect to the chamber 100. To help indicate to the user what the predetermined rotational position is for each portion of the second cap 132 with respect to chamber 100, a visual indicia 140 may be provided on (each portion of) the cap 132 as required, as shown in FIGS. 5B and 5C.

In some embodiments, the alignment mechanism may comprise at least one, or a plurality of, collar member that is rotatable with respect to the one of the caps and the chamber, wherein the alignment mechanism is configured to prevent the cap from being uncoupled from the chamber unless the at least one collar member is rotated to a predetermined position with respect to the cap and the chamber. In some of these embodiments, the one of the caps may be the cap for the first opening, wherein each collar member comprises an electrically conductive portion for transferring electrical power between the aerosol generating component and the cap for the first opening when the cap for the first opening is coupled to the chamber.

Figure 6A:
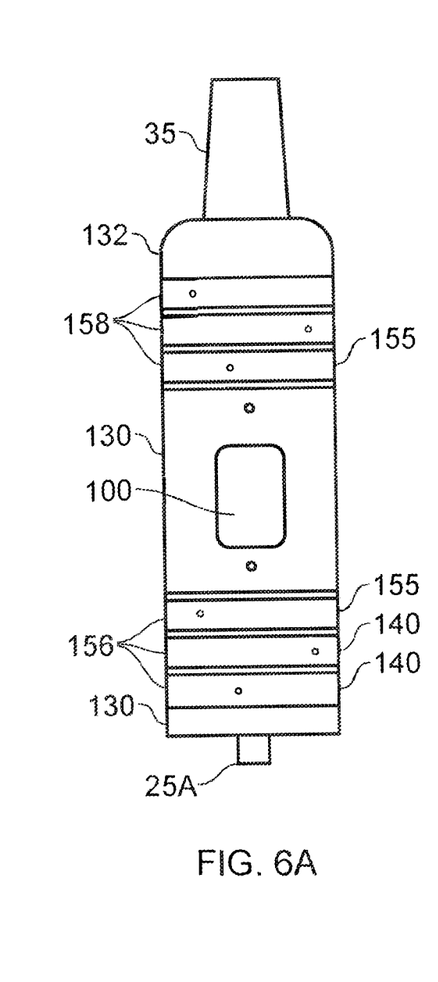
FIG. 6A is a side view of yet another exemplary aerosol provision cartridge for an aerosol provision system when in a first state.
Figure 6B:
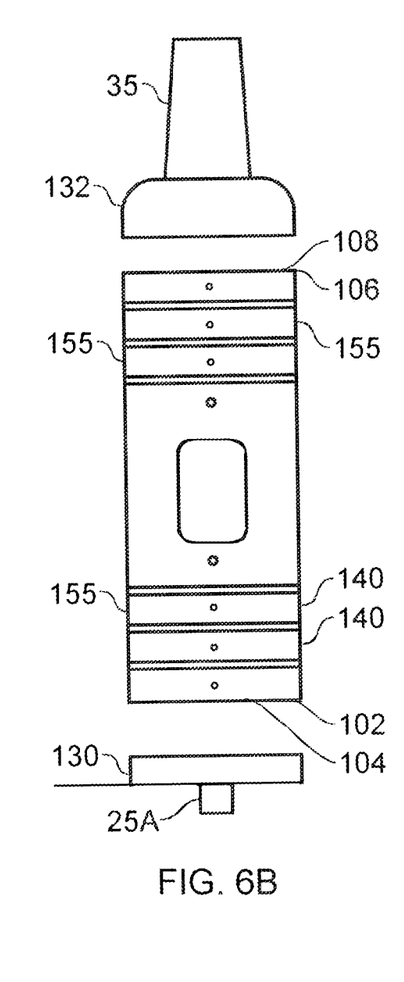
FIG. 6B is a side view of the aerosol provision cartridge from FIG. 6A when operated in a first configuration.
Figure 6C:
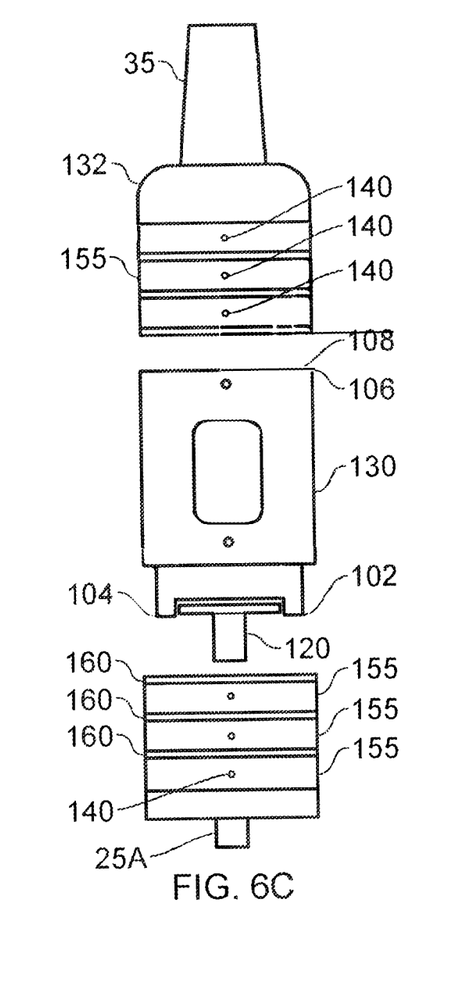
FIG. 6C is a side view of the aerosol provision cartridge from FIG. 6A when operated in a second configuration.

An example of such embodiments comprising the at least one collar member 155 is illustrated in FIGS. 6A-6C, which shows a first plurality of collar members 156 between the first cap 130 and the chamber 100, and a second plurality of collar members 158 between the second cap 132 and the chamber 100. In the embodiment shown in FIG. 6B, the first and second plurality of collar members 156;158 form part of the chamber 100, whereas in the embodiment shown in FIG. 6C, the first and second plurality of collar members 156;158 form part of the first and second caps 130;132 respectively.

Each collar member 155 is configured to require an external (intentional) force to move it. In other words, each collar member is not configured to freely move. To allow the first cap to be removed 130, each collar member 155 from the first plurality of collar members 156 must be rotated to a predetermined position with respect to the first cap 130 and the chamber. To help indicate to the user what the predetermined rotational position should be for each such collar member, in some embodiments each such collar member may comprise a visual indicia 140 (which are shown as being aligned in FIG. 6B or FIG. 6C when the collar members are together orientated at the correct rotational position). Similarly, for removal of the second cap 132, each collar member from the second plurality of collar members 158 must be rotated to a predetermined position with respect to the second cap 132 and the chamber 100.

At least in relation to the collar members from the first plurality of collar members 156, each collar member therefrom may comprise an electrically conductive portion 160 for transferring electrical power between the aerosol generating component 120 and the first cap 130, noting in these embodiments that the first cap 130 would comprise the connection 25A which receives electrical power from the corresponding connection 25B from the body 20.

In some embodiments, each collar member 155 from the alignment mechanism may have the same shape, such that any predetermined number of collar members may be used in each of the first and second plurality of collar members 156;158, and such that each collar member 155 may be used interchangeably in either the first plurality of collar members 156 or the second plurality of collar members 158. Alignment mechanisms aside, it will also be appreciated that in some embodiments, at least one, or both, of the caps 130;132 may remain attached to the chamber 100 when it is uncoupled from the chamber 100. For instance, in one particular embodiment, a connecting member may be connected between each cap 130;132 and the chamber 100 such that when the cap is uncoupled from the chamber, the cap remains attached to the chamber via the connecting member. In one particular embodiment, the connecting member may be a short cord or resilient member such that the cap may dangle freely (yet remain attached to the chamber) in relation to the chamber when it is uncoupled therefrom.

Thus, described above are examples of aerosol provision systems that can inhibit leakage of aerosol precursor material caused by inadvertent user access to the aerosol precursor material-holding region of such systems.

In order to address various issues and advance the art, this disclosure shows by way of illustration various embodiments in which the disclosure may be practiced. The advantages and features of the disclosure are of a representative sample of embodiments only, and are not exhaustive or exclusive. They are presented only to assist in understanding and to teach the disclosure. It is to be understood that advantages, embodiments, examples, functions, features, structures, or other aspects of the disclosure are not to be considered limitations on the disclosure as defined by the claims or limitations on equivalents to the claims, and that other embodiments may be utilised and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other embodiments not presently claimed, but which may be claimed in future.

The invention claimed is:

1. An aerosol provision cartridge for an aerosol provision system, wherein the cartridge comprises a refillable chamber for aerosol precursor material, the chamber comprising a first opening and a second opening, each opening allowing for access into the chamber, wherein each opening is covered by a respective cap which is configured to be uncoupled from the chamber for allowing access to the opening, wherein the cartridge is configured such that each cap, when coupled to the chamber, requires at least two different actions to be uncoupled from the chamber,
    wherein the cartridge further comprises an aerosol generating component located in the chamber;
    wherein the cap for the first opening includes an orifice through which the aerosol generating component projects when the cap for the first opening is coupled to the chamber; and
    wherein the aerosol provision cartridge further comprises a retaining means configured to hold the aerosol generating component inside the chamber when the cap for the first opening has been uncoupled from the chamber.

2. The aerosol provision cartridge according to claim 1, wherein the at least two actions are in two different directions.

3. The aerosol provision cartridge according to claim 1, wherein the aerosol generating component is removable through at least one of the first and second openings when the cap for the first opening and the cap for the second opening are uncoupled from the chamber.

4. The aerosol provision cartridge according to claim 1, wherein the aerosol generating component is removable through at least one of the first and second openings when a corresponding one of the cap for the first opening and the cap for the second opening is uncoupled from the chamber.

5. The aerosol provision cartridge according to claim 1, wherein the cap for the second opening defines a mouthpiece.

6. The aerosol provision cartridge according to claim 1, wherein the aerosol precursor material comprises a liquid.

7. The aerosol provision cartridge according to claim 1, wherein each cap remains attached to the chamber when the cap is uncoupled from the chamber.

8. The aerosol provision cartridge according to claim 1, wherein the at least two actions includes a first action which comprises: rotating; pulling; pushing; or unlatching.

9. The aerosol provision cartridge according to claim 1, wherein the at least two actions defines a second action which comprises: rotating; pulling; pushing; or unlatching.

10. The aerosol provision cartridge according to claim 1, wherein the at least two actions for the cap for the first opening is different from the at least two actions for the cap for the second opening.

11. The aerosol provision cartridge according to claim 1 wherein, for the cap for the first opening, the first action comprises pulling, and the second action comprises rotating.

12. The aerosol provision cartridge according to claim 1 wherein, for the cap for the second opening, the first action comprises pushing, and the second action comprises rotating.

13. The aerosol provision cartridge according to claim 1, wherein the chamber is substantially cylindrical.

14. The aerosol provision cartridge according to claim 13, wherein the chamber comprises a first end comprising the first opening, and comprises a second end comprising the second opening.

15. The aerosol provision cartridge according to claim 1, further comprising an alignment mechanism configured to prevent one of the caps from being uncoupled from the chamber unless the cap is rotated to a predetermined position with respect to the chamber.

16. The aerosol provision cartridge according to claim 1, further comprising an alignment mechanism configured to prevent one of the caps from being uncoupled from the chamber, wherein the alignment mechanism comprises at least one collar member that is rotatable with respect to the one of the caps and the chamber, wherein the alignment mechanism is configured to prevent the cap from being uncoupled from the chamber unless the at least one collar member is rotated to a predetermined position with respect to the cap and the chamber.

17. The aerosol provision cartridge according to claim 16, wherein the alignment mechanism comprises a plurality of collar members.

18. The aerosol provision cartridge according to claim 16, wherein the cartridge further comprises an aerosol generating component located in the chamber, wherein the one of the caps is the cap for the first opening, wherein each collar member comprises an electrically conductive portion for transferring electrical power between the aerosol generating component and the cap for the first opening when the cap for the first opening is coupled to the chamber.

19. The aerosol provision cartridge according to claim 1, further comprising a biasing means for biasing one of the caps towards a position where the cap is coupled to the chamber.

20. The aerosol provision cartridge according to claim 19, wherein the biasing means is positioned between the one of the caps and the chamber.

21. An aerosol provision system configured to receive the aerosol provision cartridge of claim 1.

22. The aerosol provision system according to claim 21, wherein the aerosol provision system comprises a body to which the aerosol provision cartridge is attachable, wherein the cap for the first opening is configured to abut the body when the cartridge is attached to the body.

23. The aerosol provision system according to claim 22, wherein the body is configured to push the cap for the first opening against the first action of the cap for the first opening when the cartridge is coupled to the body, wherein the first action of the cap for the first opening comprises pulling.

24. An aerosol provision system comprising the aerosol provision cartridge of claim 1.

25. The aerosol provision cartridge according to claim 1, further comprising visual indicia for indicating how to uncouple each cap from the chamber.

26. The aerosol provision cartridge according to claim 25, wherein the visual indica are located on the first cap and the second cap.

27. The aerosol provision cartridge according to claim 25, wherein the visual indicia comprises a series of numbered arrows on each cap.

28. A method of accessing a chamber for aerosol precursor material comprised in an aerosol provision cartridge for an aerosol provision system, wherein the aerosol provision cartridge comprises the chamber for aerosol precursor material, the chamber comprising a first opening and a second opening each allowing for access into the chamber, wherein each opening is covered by a respective cap which is configured to be uncoupled from the chamber for allowing access to the opening, wherein the aerosol provision cartridge is configured such that each cap, when coupled to the chamber, requires at least two different actions to be uncoupled from the chamber;

wherein the cartridge further comprises an aerosol generating component located in the chamber;

wherein the cap for the first opening includes an orifice through which the aerosol generating component projects when the cap for the first opening is coupled to the chamber;

wherein the aerosol provision cartridge further comprises a retaining means configured to hold the aerosol generating component inside the chamber when the cap for the first opening has been uncoupled from the chamber, and wherein the method comprises the steps of:

performing a first action on one of the caps; and performing a second action on the cap;

wherein the first action is different to the second action.

29. The method according to claim 28, wherein the method further comprises the steps of:

performing the first action in a first direction; and performing a second action in a second direction;

wherein the first direction is different to the second direction.

30. The method according to claim 28, wherein the method further comprises the steps of:

performing a third action on another of the caps in a third direction; and performing a fourth action on the another of the caps in a fourth direction;

wherein the third action is different to the fourth action, and the third direction is different to the fourth direction.

* * * * *